United States Patent
Ward et al.

(10) Patent No.: US 9,603,932 B2
(45) Date of Patent: *Mar. 28, 2017

(54) INTRAVAGINAL RING COMPRISING POLYURETHANE COMPOSITION FOR DRUG DELIVERY

(71) Applicant: DSM IP ASSETS B.V., TE Heerlen (NL)

(72) Inventors: Robert S. Ward, Orinda, CA (US); Shanger Wang, AA Echt (NL); Li Li, AA Echt (NL); Durgaprasad Chalasani, AA Echt (NL); Patrick Kiser, Salt Lake City, UT (US); Meredith Roberts Clark, Arlington, VA (US)

(73) Assignee: DSM IP ASSETS, B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/993,826

(22) Filed: Jan. 12, 2016

(65) Prior Publication Data

US 2016/0120800 A1    May 5, 2016

Related U.S. Application Data

(63) Continuation of application No. 13/885,665, filed as application No. PCT/EP2011/070164 on Nov. 15, 2011, now Pat. No. 9,393,311.

(60) Provisional application No. 61/413,929, filed on Nov. 15, 2010.

(51) Int. Cl.
| | |
|---|---|
| *A61K 9/00* | (2006.01) |
| *A61K 47/34* | (2017.01) |
| *A61K 31/341* | (2006.01) |
| *A61K 31/675* | (2006.01) |

(52) U.S. Cl.
CPC ............ *A61K 47/34* (2013.01); *A61K 9/0036* (2013.01); *A61K 31/341* (2013.01); *A61K 31/675* (2013.01)

(58) Field of Classification Search
CPC .... A61K 47/34; A61K 9/0036; A61K 31/341; A61K 31/675
See application file for complete search history.

(56) References Cited

U.S. PATENT DOCUMENTS

| | | | | |
|---|---|---|---|---|
| 4,523,005 | A | * 6/1985 | Szycher | ............ C08G 18/4854 528/76 |
| 5,756,632 | A | 5/1998 | Ward et al. | |
| 2007/0128154 | A1* | 6/2007 | Hadba | ................ A61L 24/0042 424/78.27 |
| 2014/0045792 | A1* | 2/2014 | Ward | ................... A61K 9/0036 514/81 |

FOREIGN PATENT DOCUMENTS

| | | | |
|---|---|---|---|
| WO | 2004/044012 A1 | 5/2004 | |
| WO | WO2004/044012 | * 5/2004 | |
| WO | 2009/003125 A1 | 12/2008 | |
| WO | 2009/094573 A1 | 7/2009 | |
| WO | WO2009/094573 | * 7/2009 | ............ A61M 31/00 |

OTHER PUBLICATIONS

Evan Hetrick & Mark Schoenfisch, Reducing Implant-Related Infections: Active Release Strategies, 35 Chem. Soc. Rev. 780, 782 (2006).*
Anne Simmons, et al, Biostability and Biological Performance of a PDMS-based Polyurethane for Controlled Drug Release, 29 Biomat. 2987, 2988 (2008).*
Anne Simmons, et al, Biostability and Biological Performance of a PDMS-based Polyurethane for Controlled Drug Release, 29 BIOMAT. 2987-2988 (2008).
Johnson, T. J. et al., "Segmented polyurethane intravaginal rings for the sustained combined delivery of antiretroviral agents dapivirine and tenofovir," European Journal of Pharmaceutical Sciences, Elsevier, Amsterdam, NL, vol. 39, No. 4, Feb. 19, 2010, pp. 203-212.

* cited by examiner

*Primary Examiner* — Sean Basquill
(74) *Attorney, Agent, or Firm* — Kevin M. Bull

(57) ABSTRACT

Intravaginal drug delivery device comprising at least one pharmaceutically active substance, and a polyurethane copolymer, wherein the copolymer has the structure according to formula (I):

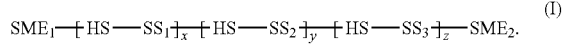

Also, method comprising administering one or more pharmaceutically active substances to a patient in need thereof.

10 Claims, No Drawings

INTRAVAGINAL RING COMPRISING POLYURETHANE COMPOSITION FOR DRUG DELIVERY

This application is a continuation of application Ser. No. 13/885,665, filed Oct. 30, 2013. Ser. No. 13/885,665 is the National Phase under 35 U.S.C. §371 of International Application No. PCT/EP2011/070164, filed Nov. 15, 2011, which claims priority to provisional application Ser. No. 61/413,929, filed Nov. 15, 2010. The entire contents of all applications listed above are incorporated by reference herein.

BACKGROUND OF THE INVENTION

The present invention relates to intravaginal drug delivery devices made of polyurethane copolymers and to administering one or more pharmaceutically active substances to a patient in need thereof.

Drug delivery devices are specialized tools for the delivery of a drug or therapeutic agent via a specific route of administration. Such devices are used as part of one or more medical treatments. Examples of drug delivery devices include, but are not limited to, cardiovascular devices, ophthalmic devices, antivirus devices, dialysis devices, contraceptive devices, drug-eluting stents, catheter tubing, transdermal devices, and/or intra-uterine devices.

Drug delivery devices, such as intravaginal drug delivery devices, including intravaginal rings (IVRs), are typically formed from biocompatible polymers and contain a drug released by diffusion through the polymer matrix. The IVR devices may be inserted into the vaginal cavity and the drug may be absorbed by the surrounding body fluid through the vaginal tissue.

Poly(ethylene-co-vinyl acetate), or ethylene vinyl acetate (EVA) (used e.g. in NuvaRing), and poly(dimethyl siloxane), or silicone (used e.g. in Estring, Femring and in Population Councils progesterone-releasing ring), are currently commercially exploited for IVRs. Compared to poly(ethylene-co-vinyl acetate) or ethylene vinyl acetate (EVA), silicone is limited by a lower mechanical stiffness. Therefore, silicone IVRs are fabricated with larger cross-sectional diameters to achieve the retractive forces required for retention in the vaginal cavity, which may affect ring user acceptability. Moreover, the manufacturing costs associated with these IVRs are considerable. Both EVA and silicone have been found particularly useful for the release of a steroid which is a substantially water-insoluble drug.

Polyurethane-containing intravaginal rings have been described (See, Gupta, Kavita M. et all. Journal of Pharmaceutical Sciences (2008), 97(10), 4228-4239 and, and WO2009094573. The known polyurethane-containing IVRs are IVRs containing one single drug. Further, segmented polyurethane IVRs are described in WO2009003125 and WO2009094573.

In addition, the use of polyurethanes for drug delivery devices has been limited in part due to the high processing temperatures required for polyurethanes. These temperatures are often too high for thermolabile drugs.

It has also been found that EVA and silicone, which are both hydrophobic polymers, are not able to provide a desired release rate for hydrophilic drugs. So far, no intravaginal ring has been developed for the co-delivery of drugs with different hydrophilicity.

BRIEF SUMMARY OF THE INVENTION

This deficiency is remedied by the presently disclosed intravaginal drug delivery devices. Drug delivery devices, including intravaginal rings, comprising polyurethane copolymers are provided by the present invention. Unlike the drug delivery devices according to the prior art the present drug delivery devices can provide adequate release rates for multiple drugs. Another advantage of the drug delivery devices according to the invention is that the devices comprise a biostable polymer, which is used as a matrix to disperse or dissolve the drug within.

A further advantage of the drug delivery devices according to the invention is that the release characteristics of the polyurethane in the drug delivery device can be tailored to accommodate a range of suitable pharmaceutically active substances to be delivered from the drug delivery product.

A further advantage is that the polyurethane copolymers comprised in the drug delivery device can have lowered processing temperatures.

A further advantage is that the polyurethane copolymer comprised in the drug delivery device has a tunable permability to pharmaceutical active compounds which are diffused throughout the polymer matrix. This permability depends on the characteristics of the polymer matrix, such as the hydrophilicity of the various blocks or segments of the co-polymer.

DESCRIPTION OF THE INVENTION

The present invention relates to drug delivery devices comprising at least one pharmaceutically active substance and a polyurethane copolymer.

The polyurethane copolymers in the drug delivery device according to the invention are copolymers with a structure according to formula I:

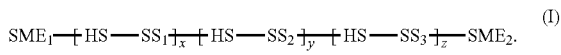

wherein,
SME1 and SME2 can be the same or different and denote a surface modifying endgroup, having a number average molecular weight ranging from 200 to 8000, linked to the polymer via a urethane or urea bond resulting from the reaction of an amine- or alcohol-terminated surface modifying endgroup with an isocyanate group;
SS1, SS2, and SS3 denote soft-segments, wherein
SS1 is a polyether diol selected from polyethylene oxide (PEO) diol, polytetramethylene oxide (PTMO) diol, polyhexamethylene oxide diol (PHMO), polypropylene oxide (PPO) diol, copolymer of ethylene glycol and propylene glycol (PEG-co-PPO) diol, and mixtures thereof;
SS2 is a hydroxyl or amine-terminated silicone polymer having a number average molecular weight ranging from 500 to 5000 g/mol; and
SS3 is a soft-segment selected from polycarbonate diol and polyester diol, and mixtures thereof;
HS denotes a hard-segment prepared from the reaction of one or more diisocyanates and one or more chain extenders,
x, y and z are the same or different and each is an integer equal to or greater than zero and at least one of x, y and z is not zero; and
wherein the copolymer has a number average molecular weight ranging from 50,000 to 350,000 g/mol.

The drug delivery devices according to the invention comprise at least one pharmaceutically active substance. Pharmaceutically active substances which can be incorporated into the drug delivery devices comprising the copolymers include microbicides, contraceptive agents, estrogen receptor modulators, post-menopausal hormone, antiretroviral, anticancer, therapeutic agents, hormones, and combinations thereof. Examples of hydrophobic pharmaceutically active substances include but are not limited to dapivirine, UC781, valdecoxib, allopurinol, acetohexamide, benzthiazide, chlorpromazine, chlordiazepoxide, haloperidol, indomethacine, lorazepam, methoxsalen, methylprednisone, nifedipine, oxazepam, oxyphenbutazone, prednisone, prednisolone, pyrimethamine, phenindione, sulfisoxazole, sulfadiazine, temazepam, sulfamerazine, trioxsalen. Examples of hydrophilic pharmaceutically active substances include but are not limited to 17β-Estradiol, Aciclovir, Estriol, Raloxifene, Pravastatin, Atenolol, aminoglycosides, polysaccharide, cyclodextrins and chitosan.

In the present instance, hydrophilicity of a drug or a copolymer block is determined by the solubility in water at 25° C. If a chemical has a solubility value of less than 0.01 mg/ml in water at 25° C., it is considered hydrophobic. If a chemical has a solubility value of above 0.01 mg/m in water at 25° C., it is considered to be hydrophilic.

In one embodiment the drug delivery devices comprise an anti-HIV agent selected from the group consisting of non-nucleoside reverse transcriptase inhibitors, nucleoside reverse transcriptase inhibitors, and HIV entry inhibitors. Preferably, the non-nucleoside reverse transcriptase inhibitor is UC 781 and/or the nucleoside reverse transcriptase inhibitor is Tenofovir.

The present drug delivery devicess preferably comprises at least two pharmaceutically active substances in a single copolymer. In particular they can accommodate two pharmaceutically active substances having contrasting hydrophilicities. Thus, the drug delivery device has been developed for the co-delivery of pharmaceutically active substances with contrasting hydrophilicity from one polymer. The drug delivery device can be a medical device, such as intravaginal ring. The drug delivery devices are tailored to codeliver pharmaceutically active substances with contrasting hydrophilicity from a polyurethane copolymer which forms a single segment drug delivery device. In the case of intravaginal rings, the single segment IVR device should be more easily-manufactured and less costly than the multisegment IVR (see Todd J. Johnson, et al., "Segmented polyurethane intravaginal rings for the sutained combined delivery of antiretroviral agents dapivirine and tenofovir" European Journal of Pharmaceutical Sciences 39 (2010) 203-207, which describes two drugs, dapivirine and tenofovir with contrasting hydrophilicity being delivered from a dual segment IVR device. The two drugs were separately formulated into polyurethanes with matching hydrophilicity. The drug loaded rods were then joined together to form dual segment IVRs).

Preferably, the drug delivery device comprises two or more pharmaceutically active substances. In this instance, the pharmaceutically active substances can have the same hydrophilicity or hydrophobicity or different hydrophilicities or hydrophobicities.

In one embodiment, the amount of pharmaceutically active substance to be incorporated into the drug delivery devices ranges from about 0.005 to about 65 weight % related to the total weight of the polyurethane copolymer in the drug delivery device, and more preferably ranges from about 0.2 weight % to about 30 weight % of the polyurethane copolymer in the drug delivery device. The amount of pharmaceutically active substance incorporated can also be calculated as a pharmaceutically effective amount, where the devices of the present polyurethane copolymer comprise a pharmaceutically effective amount of one or more pharmaceutically active substances. By "pharmaceutically effective," it is meant an amount which is sufficient to effect the desired physiological or pharmacological change in subject. This amount will vary depending upon such factors as the potency of the particular pharmaceutically active substance, the desired physiological or pharmacological effect, and the time span of the intended treatment. Those skilled in the pharmaceutical arts will be able to determine the pharmaceutically effective amount for any given pharmaceutically active substance in accordance with the standard procedure. In some embodiments, the pharmaceutically active substance is present in an amount ranging from about 2 mg to about 300 mg of pharmaceutically active substance per gram of polyether urethane. This includes embodiments in which the amount ranges from about 2 mg to about 50 mg, from about 50 mg to about 150 mg, and from about 150 mg to about 300 mg of pharmaceutically active substance per gram of polyether urethane.

The drug delivery device according to the invention comprises at least one polyurethane copolymer with a structure according to formula (I).

The soft segments of the polyurethane copolymer according to formula (I) comprise a diol. A diol is an alcohol containing at least two hydroxyl groups. A diol is a polymeric soft segment which is distinguished from short chain or low-molecular weight chain extenders. The diols of the soft segments of the polyurethane copolymers of the present invention contain at least two hydroxyl groups. Examples of polyether diols (SS1), which are considered hydrophilic diols, are PEO diol, PTMO diol, PPO diol, copolymer of PPO-co-PEO diol, Examples of hydrophobic diols include silicone diols (SS2), polyester diols, or polycarbonate diols (SS3).

In general the number average molecular weights of the soft segments ranges from 500 to 5000 g/mol.

In the present polyurethane copolymers, there are three blocks which comprise the soft segment; SS1, SS2, and SS3. The ratio of the soft segments may characterize the structural features of the present polymers. For instance, if x=0, y=1, and z=2, then SS1 is not present and the ratio of SS3 to SS2 is 2 to 1.

In one embodiment, SS1 is a polyether diol selected from PEO diol, PTMO diol, polyhexamethylene oxide diol (PHMO), PPO diol, copolymer of ethylene glycol and propylene glycol (PEG-co-PPO diol), and mixtures thereof.

The PEO diol may be a linear PEO diol or a side-chain PEO diol. The side-chain PEO diol may be YMER®N120.

In one embodiment, SS2 is a hydroxyl or amine-terminated silicone polymer.

The addition of silicone soft segments which are hydrophobic in nature can modify the release characteristics of the drug. Silicone soft segments include silicone diols having a number average molecular weight ranging from 500 to 5000. Examples of which may include silicone polymers prepared by using silicones like ShinEtsu's X22-160 AS (Molecular Weight~1000) and MCR-C61 (Molecular Weight~1000), or PDS-1615 (Molecular Weight~900-1000) of Gelest.

The percentage of the silicone soft segment can be up to 40 weight %, or more preferably may be up to 20 weight % of the total weight of the polyurethane copolymer.

SS3 is a soft-segment other than polyether and silicone and is selected from polycarbonate diol, polyester diol and mixtures thereof.

In one embodiment, the polyurethane copolymer comprises at least two different soft segments.

In the polyurethane copolymers, the hard segment, HS, can be made from the reaction of diisocyanate and chain extender. For the purpose of the polyurethane copolymers according to formula 1, a diisocyanate is a molecule with two isocyanate functional groups, R—(N═C═O)$_{n=2}$.

Diisocyanates can be aromatic or aliphatic diisocyanates. Aliphatic diisocyanates are preferably used in the polyurethane copolymers according to the invention. Aliphatic diisocyanates include, but are not limited to hexamethylene diisocyanate (HMDI) and isophorone diisocyanate (IPDI) and combinations thereof.

A chain extender can be selected from short chain diol, diamine, or amino alcohol having a number average molecular weight ranging from 32 to 500, or can be a side chain PEO wherein the diol is on one side of the molecular chain, such as in YMER®N120, having a number average molecular weight ranging from 500 to 3000 g/mol, and mixtures thereof. Examples of the short chain diol include, but are not limited to, ethylene glycol, 1,4-butanediol (1,4-BDO or BDO), 1,6-hexanediol, cyclohexane dimethanol and hydroquinone bis(2-hydroxyethyl) ether (HQEE).

In one embodiment the percentage of the hard segment can range from 20 to 45 weight % of the total weight of the polyurethane copolymer.

The polymers according to the invention comprise a surface modifying agent or surface modifying endgroup (SME), into the polymer. A surface modifying endgroup is an endgroup that spontaneously rearranges its positioning in a polymer body to position the endgroup on the surface of the body depending upon the composition of the medium with which the body is in contact.

In one embodiment surface modifying endgroups may be selected from amine- or alcohol-terminated polyalkylene oxides, silicones, alkyl, alkylesters, polyalkylene esters and mixtures thereof.

Other surface modifying endgroups include alkyl chains, fluorinated alkyl chains, polyether, fluorinated polyether, silicone, and those described in U.S. Pat. No. 5,589,563, which is hereby incorporated by reference in its entirety.

A preferred SME group that can be used in the polyurethane copolymers according to the present invention is methyl polyethylene glycol (MPEG).

The endgroups migrate to the surface of a device and thereby introduce a biocompatible surface without compromising the bulk properties of the polymer. For example, MPEG dominates the IVR surface which results in a non-fouling surface and facilitates drug release by reducing deposit formation.

x, y and z in Formula I are integers equal to or greater than zero. Preferred integers are greater than zero and lower than 700, preferably lower than 200. At least one of x, y and z in formula 1 is not equal to zero.

In one embodiment, the polyurethane copolymer comprises 15-35 weight % of at least one soft segment, 20-40 weight % of at least one hard segment and 0-2 weight % of a surface modifying endgroup; all related to the total weight of the dry polyurethane copolymer.

In an embodiment of the invention the polyurethane copolymers in the drug delivery device are capable of absorbing water up to 50 weight % related to the total weight of the dry copolymer.

Antioxidants and other additives can be added to the present polyurethane copolymers in the drug delivery device. Examples of antioxidants include but not limited to octadecyl-3-(3,5-di-tert.butyl-4-hydroxyphenyl)-propionate (Irganox®), ethylenediaminetetraacetic acid (EDTA), butylated hydroxytoluene (BHT), citric acid (CA), butylated hydroxyanisole (BHA), tertiary butylhydroquinone (TBHQ), and propyl gallate (PG).

In one embodiment, the polydispersity index ($M_w/M_n$) of the present urethane copolymers can range from approximately 1.5 to 2.5.

The polyurethanes are biocompatible. By biocompatible it is meant that a biomaterial is able to perform its desired function with respect to a medical therapy, without eliciting any undesirable local or systemic effects in the recipient.

Specifically, the present polyurethanes are non-cytotoxic to a vaginal cell line such as Vk2.

The polyurethane copolymers used in the drug delivery devices according to the invention are produced in a polyurethane production process.

The process involves producing polyurethanes by the polyaddition reaction of one or more diisocyanates with one or more diols, one or more chain extenders and one or more surface modifying endgroups in the presence of a catalyst. The reaction product is a polymer containing the urethane linkage, —RNHCOOR'—. A generalized polyurethane reaction is as shown below:

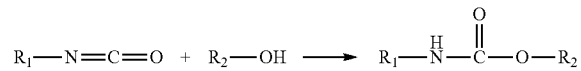

The catalyst can include organo tin compounds, bismuth compounds, organic and inorganic bases, and combinations thereof. Specific examples include dibutylin dilaurate, stannous octoate, and combinations thereof. The catalyst is preferably stannous octoate.

Preferably, a polyurethane copolymer is mixed or extruded with at least one pharmaceutically active substance or pharmaceutically active substance to form a pharmaceutically active substance-loaded polyurethane copolymer. The methods of mixing include compounding polyurethane with pharmaceutically active substance, dissolving both polyurethane and pharmaceutically active substance in solution followed by evaporation of solvent.

Extrusion conditions of the polyurethane copolymers are below 240° C., preferably below 160° C. and more preferably between 128° C.-155° C. in order to retain pharmaceutically active substance stability for thermolabile pharmaceutically active substances. Polyurethane copolymers comprising aliphatic diisocyanates can be extruded at these low temperatures.

The pharmaceutically active substance-loaded polyurethane copolymer is formed into shapes suitable for use in drug delivery, wherein a pharmaceutically effective amount of at least one pharmaceutically active substance is homogeneously distributed throughout the copolymer. This may be carried out under a variety of conditions, including, but not limited to those described in Example 1.

The polyurethane copolymer forms a polymer matrix and preferably, the polymer matrix forms a monolithic system. In this way a single segment, monolithic drug delivery device can be formed from the polyurethane copolymer.

The pharmaceutically active substance-loaded polyurethane copolymer is formed into a shape suitable for use in intravaginal drug delivery, wherein a pharmaceutically effective amount of at least one vaginally administrable pharmaceutically active substance is compounded with the polyurethane copolymer. In some embodiments in which the device is an intravaginal ring, the step of forming the pharmaceutically active substance-loaded polyether urethane copolymer into the shape of the device involves extruding the pharmaceutically active substance-loaded polyurethane copolymer into a rod and joining the ends of the extruded rod to form a ring. The ends of the ring may be joined together via a variety of biocompatible adhesives, including, but not limited to molten pharmaceutically active substance-free or pharmaceutically active substance-loaded polyurethane. Each of these steps may be carried out under a variety of conditions.

The drug delivery devices of the present invention may encompass a variety of shapes and sizes provided the device is compatible with internal administration to the subject and with the requirements imposed by drug delivery kinetics. The dimensions of the of the device may vary depending upon the mode of administration, anatomy of the subject, the amount of pharmaceutically active substance to be delivered to the patient, the time over which the pharmaceutically active substance is to be delivered, the diffusion characteristics of the pharmaceutically active substance and other manufacturing considerations.

The device is for intravaginal administration. This includes embodiments, where the device is in the form of an intravaginal ring (IVR) or is in annular form. The IVR should be flexible enough to enable bending and insertion inside the vaginal cavity and rigid enough to withstand the expulsive forces of the vaginal musculature without causing abrasion to the vaginal epithelium. In some embodiments, the cross-sectional diameter of the IVRs may range, e.g., from about 3 mm to about 10 mm. Other intravaginal devices include tablets, pessaries, rods and films for adhesion to the mucosal epithelium as disclosed in U.S. Pat. No. 6,951,654, which is hereby incorporated by reference in its entirety.

The present polyurethane drug delivery devices demonstrate release characteristics which are tailored to accommodate a range of suitable pharmaceutically active substances, to provide sustained release of pharmaceutically effective amounts of pharmaceutically active substances in the desired length of usage. Specifically pharmaceutically active substances can include UC781, Tenofovir (TFV), and Levonorgestrel (LNG) alone or in combination, including combination of pharmaceutically active substances with contrasting hydrophilicity, (e.g. UC781 and Tenofovir) to be delivered from an intravaginal drug delivery device and provide a range of delivery rates for a particular pharmaceutically active substance. The release rate can be controlled through the percentage of hard segment, ratio of the hydrophilic segment to the hydrophobic segment of the polyurethane and the selection of diisocyanate.

In an embodiment the release rate of a pharmaceutically active substance is determined by a daily flux value. Preferably, the mean daily flux of at least one of the pharmaceutical active substances is greater than 0.1 μg/mm$^2$/d.

Unlike a bioresorbable drug delivery device, the device of the invention comprises a biostable polymer used as a matrix to disperse or dissolve the drug within. The polymer thus needs to support mechanical integrity and physical stability.

Properties which are desired for intravaginal drug delivery devices include mechanical properties, drug release properties, biostability and biocompatibility for the intended implantation duration. The mechanical properties (dry and swollen hardness, tensile strength, modulus, percentage elongation at break) of an IVR material are crucial to the IVR's efficacy and acceptability in vivo. An IVR that is too stiff may be difficult to insert and could cause tissue damage and inflammation. (See, Bounds, W., Szarewski, A., Lowe, D., Guillebaud, J., 1993. Preliminary report of unexpected local reactions to a progestogen-releasing contraceptive vaginal ring. Eur. J. Obstet. Gynecol. Reprod. Biol. 48, 123-125 and Weisberg, E., Fraser, I. S., Baker, J., Archer, D., Landgren, B. M., Killick, S., Soutter, P., Krause, T., D'arcangues, C., 2000 A randomized comparison of the effects on vaginal and cervical epithelium of a placebo vaginal ring with non-use of a ring. Contraception 62, 83-89.) Whereas a ring that is too soft may lack retention and thus slip or be expelled from the vagina (Koetsawang, S., Ji, G., Krishna, U., Cuadros, A., Dhall, G. I., Wyss, R., Rodriquez La Puenta, J., Andrade, A. T., Khan, T., Kononova, E. S., et al., 1990. Microdose intravaginal levonorgestrel contraception: a multicentre clinical trial. III. The relationship between pregnancy rate and body weight. World Health Organization. Task force on long-acting systemic agents for fertility regulation. Contraception 41, 143-150). Since the device is used in vaginal environment it is important for the polymer to show desired mechanical properties after the polymer is swollen by vaginal fluid. Therefore, swollen hardness (in pH 4.0 buffer simulating the vaginal environment) of the polymer was also one of the design criteria.

The intravaginal devices should be capable of providing sustained delivery of one or more pharmaceutically active substances for the desired length of usage. The drug release rate is affected by the percent equilibrium swelling of the polymer. For example, for a hydrophilic pharmaceutically active substance, the release rate should increase with the increase of percentage of equilibrium swelling of the polymer.

A further embodiment of the invention is a method for administering one or more pharmaceutically active substances to a patient in need thereof, comprising inserting the drug delivery device into the patient, whereby the active substance is released from the delivery device while the device resides in a subject's body.

The invention will now be illustrated by the following, non-limiting examples.

EXAMPLES

Mechanical properties which are desired for medical devices in general include hardness, tensile strength, modulus, percentage elongation at break.

Hardness may be measured either dry, or with swollen polymers. In any case, the hardness should be at least 30 A. Dry hardness may preferably range from 40 A-45 D. Swollen hardness may preferably range from 30 A to 90 A. The hardness of the polymer is measured by the Shore® test. The Shore hardness is measured with an apparatus known as a Durometer and consequently is also known as 'Durometer hardness'. The hardness value is determined by the penetration of the Durometer indenter foot into the sample.

The tensile strength of the present polymers may range from 115.0 psi to 5400.0 psi. A preferred tensile strength is at least 500 psi.

A measurement of the stiffness may be the Young's modulus.

Properties which are desired for intravaginal drug delivery devices include mechanical properties, drug release properties, biostability and biocompability for the intended implantation duration.

Example 1

Synthesis of Polyurethanes

Several batches of polyurethane material are synthesized by varying the formulation of each batch (Table 1). The compositional changes made in the various batches include 1) using either isophorone diisocyanate (IPDI) or hexamethylene diisocyanate (HMDI) as the aliphatic isocyanate, 2) changing the percentage hard segment, 3) using different amounts of methoxy polyethylene glycol (MPEG) soft segment, 4) inclusion of silicone soft segment, and 5) varying the catalyst.

Polyurethane was synthesized in a batch reactor. A batch synthesis of the polyurethane material involved adding the required quantity of polyols, aliphatic diisocyanate and catalyst to a glass quart jar equipped with a mechanical stirrer, heating the jar to 100° C. for 3 hours followed by addition of required quantity of a surface modifying endgroup and continuing heating at same temperature for 2 hours. Chain extension was achieved by addition of butanediol after which the polymeric material was poured into plastic trays and cured at 100° C. for 24 hours. The hardened polymer slab is then grinded into smaller granules for compounding with pharmaceutically active substances.

Example 2

Mw, Swelling, Mechanical, Process Temperature of Polyurethanes

The analytical results for the various polyurethane batches are summarized in Table 1. It was found that most polyurethane batches met the criteria for Mw, swelling, and dry mechanical properties that is desirable for IVR devices. The polyurethanes were compounded with 20% tenofovir (TFV) and 5% UC781. Most batches compounded with TFV and UC781 show a 2-3 fold reduction in elastic modulus when hydrated. In addition, results also showed that polyurethanes according to lot#1100032, 1100235, 1100048, and 1100234 could be used to design a IVR that has mechanical properties (force @ 25% IVR compression) similar to IVRs already in use such as NuvaRing with acceptable IVR cross-sectional diameter (~5-9 mm).

Example 3

Compounding of TFV and UC781 Loaded Polyurethanes Matrices

The polyurethanes were compounded with 20% TFV and 5% UC781. As an example, batches 1100234 and 1100235 were compounded with 20% TFV and 5% UC781 and extruded in to 5 mm cross-section cylindrical strands. Extrusion temperatures for 1100234 and 1100235 were 128° C. and 134° C., respectively. Approximately 10-20 mm long segments were incubated in 25 mM sodium acetate buffer with 2% Solutol HS-15 (pH=4.2) (changed daily) at 37° C. and 80 rpm in a heated shaker for 7 days. Samples of release media, taken after 24±1 hrs. incubation were taken and stored at −80° C. Samples were analyzed utilizing a 25-minute gradient (pH=6 potassium phosphate and acetonitrile) HPLC method. Using the model y=a*(1+x)^b, release data were fitted to a continuous profile, the equation of which was used to determine the average daily flux. Release data represent N=3 rods, mean±standard deviation (SD).

Example 4

Drug Release Studies of TFV and UC781 Loaded Polyurethanes

Approximately 15 mm long segments were incubated in 25 mM sodium acetate buffer with 2% Solutol HS-15 (pH=4.2) (changed daily) at 37° C. and 80 rpm in a heated shaker for 30 days. Samples of release media, taken after 24±1 hrs. incubation were taken and stored at −80° C. For lots '68' and '40' equal volumes of each aliquot were mixed in an HPLC vial to represent the average daily concentration of each analyte. For all other materials, aliqouts from three timepoints throughout the release study were analyzed by HPLC. Using the model y=a*(1+x)^b, release data was fitted to a continuous profile, the equation of which was used to determine the average daily flux. Release data represent N=3 rods, mean±SD.

Results showed that UC781 flux is 2-3 $\mu g/mm^2/d$ and minimally impacted by polymer composition; TFV flux ranged from 2-23 $\mu g/mm^2/d$ and was correlated with 1) degree of swelling, 2) hard segment percentage, and 3) silicone content. It was found that initial drug burst release increased with increasing hardness of the polyurethane material. This was both surprising and unexpected. In general, the initial drug burst release was expected to decrease with increasing hardness of polyurethane.

Example 5

Processing Stability and Accelerated Stability Study of TFV and UC781 Loaded Polyurethanes Lot#1100032 was compounded with TFV and UC781 and it was found that Mw decreased to 58% of the original value after extrusion (Table 2). The decrease in the molecular weight of Lot#1100032 may be mainly caused by the relatively high water content of the polymer before being extruded and the TFV (20 wt % in PU) being a monohydrate which tends to facilitate the hydrolysis of the PU material. Various antioxidants were incorporated into lot#1100032 in order to improve the process stability, and it was found that Mw still reduced to 39-61% of the original value with antioxidants (Table 2). The results suggest that antioxidants do not improve the process stability of the polyurethanes compounded with drugs.

In addition to the processing stability studies, accelerated stability study was also performed on Lot#1100032 compounded with TFV and UC781, with various antioxidants added. Samples were pulled after ~2.5 month and stability of Lot#1100032 was evaluated by Mw analyses. It was found that the Mw hardly changed after the ~2.5 months' accelerated stability study compared to the control (t=0) for all antioxidants. The results suggest that Lot#1100032 was stable in the accelerated storage conditions in the presence of the drugs and antioxidants.

Example 6

Drug Stability in TFV and UC781 Loaded Polyurethanes

The drug stability in compounded lot#1100032 was also studied after extrusion and under accelerated storage conditions, with and without various antioxidants (Table 3). The results suggest that the process flow temperature (128° C.-155° C.) of the polyurethanes were low enough to retain UC781 stability after the extrusion. The 4-5 week, 60° C. data showed that Irganox is incompatible with UC781. UC781 showed the best stability with BHT, EDTA or without any additives.

Example 7

Cytotoxicity of Polyurethanes

50±5 mg of extruded polymer rod segments (single extrusion, no cryogrinding, no drying) were dipped in 70% isopropanol for 5 seconds and air dried for about an hour in a laminar flow hood. Rods were transferred to microcentrifuge tubes and incubated in 1.5 ml of Keratinocyte-SF cell media. The tubes were allowed to rotate in the microcentrifuge at setting "8" for 24 hrs at room temperature. Pieces of latex (6-7 per tube measuring 5 mm×2 mm) were also incubated in 1.5 ml media/tube. N-9 (49.6 µM conc.) was made in media. Vk2 cells were plated at a density of 40,000 cells per well (96-well format) and incubated for 24 hrs (37 C, 5% $CO_2$). 300 µl of media from each rod-containing and latex-containing centrifuge tube is added to the cells (N=6). 300µ of N-9 in media was also added to cells (N=6). The cells were incubated for 24 hrs. A cell viability analysis using the Cell Titer 96 Aqueous Non-Radioactive Cell Proliferation Assay (MTS assay) was performed.

It was found that (see Table 1) the preliminary batches prepared with dibutyltin dilaurate as catalyst were cytotoxic to a vaginal cell line (e.g., lot#1100032). In later batches (e.g., lot#1100121), dibutyltin dilaurate was replaced by stannous octoate and the batches were found to be non-cytotoxic. The results suggest that dibutyltin dilaurate is the cause of cytotoxicity for the batches which use this catalyst and stannous octoate should be used as the catalyst.

TABLE 1

Comparison of polyurethane batches. *Daily drug flux calculated using the mixing method, all others using the curve-fitting method

| | Lot# | | | | | | | | | |
|---|---|---|---|---|---|---|---|---|---|---|
| | 1100032 | 1100040 | 1100048 | 1100068 | 1100121 | 1100234 | 1100235 | 1100092 | 1100096 | 1100114 |
| Diisocyanate | HMDI | HMDI | HMDI | IPDI | HMDI | HMDI | HMDI | HMDI | HMDI | HMDI |
| % PEG 1450 | 20 | 32.6 | 20 | 20 | 20 | 20 | 20 | 20 | 20 | 15 |
| ShinEtsu 160AS (MW ~1000) | 0 | 0 | 0 | 0 | 0 | 0 | 0 | 20 | 10 | 10 |
| % MPEG | 0.5 | 0.5 | 0.5 | 0.5 | 0.5 | 0.5 | 0.5 | 0.5 | 0.5 | 0.5 |
| % Hard segment | 35 | 24 | 24 | 35 | 35 | 24 | 30 | 35 | 35 | 35 |
| Catalyst | 400 ppm dibutyltin dilaurate | 640 ppm dibutyltin dilaurate | 215 ppm dibutyltin dilaurate | 553 ppm dibutyltin dilaurate | 205 ppm stannous octoate | 446 ppm stannous octoate | 449 ppm stannous octoate | 308 ppm dibutyltin dilaurate | 308 ppm dibutyltin dilaurate | 231 ppm dibutyltin dilaurate |
| Test Results | Result | Result | Result | Result | Result | Result | Result | Result | Result | Result |
| Dry Hardness | 69.3A | 54.2A | 54.2A | 54.6A | 67.0A | 54.6A | 64.0A | 71.2A | 72.4A | 70.4A |
| Swollen Hardness, after incubation in pH 4.0 buffer at 37° C. | 64.4A | 42.2A | 55.0A | 39.4A | 68.8A | 55.2A | 63.8A | 67.2A | 67.0A | 68.6A |
| GPC - Mn, number average molecular weight | 193088 | 198344 | 110630 | 158064 | 81901 | 119000 | 107400 | 147720 | 166072 | 81366 |
| GPC - Mw, weight average molecular weight | 395574 | 397345 | 228304 | 311910 | 127514 | 245700 | 229700 | 283705 | 354421 | 145804 |
| GPC - Polydispersity index (Mw/Mn) | 2.05 | 2.00 | 2.07 | 1.97 | 1.56 | 2.065 | 2.14 | 1.92 | 2.14 | 1.79 |
| Tensile Strength @ Break | 2119.7 psi | 1113.6 psi | 271.6 psi | 113.5 psi | 1647.1 psi | 1052.12 psi | 642.68 psi | 1333.6 psi | 2351.7 psi | 861.7 psi |
| Secant Modulus @ 50% | 772.8 psi | 315.2 psi | 245.6 psi | 154.56 psi | 821.3 psi | 236.25 psi | 316.40 psi | 449.9 psi | 471.6 psi | 594.5 psi |
| Secant Modulus @ 100% | 557.1 psi | 209.1 psi | 165.0 psi | 89.01 psi | 609.4 psi | 163.90 psi | 229.31 psi | 331.2 psi | 342.4 psi | 433.7 psi |
| Secant Modulus @ 300% | 342.1 psi | 104.4 psi | 78.4 psi | 23.62 psi | 361.3 psi | 93.19 psi | 147.09 psi | 234.9 psi | 238.5 psi | 281.7 psi |
| Percentage Elongation at Break | 600.60% | 836.70% | 381.10% | 1994.70% | 533.50% | 868.60% | 464.60% | 547.90% | 726.20% | 325.10% |
| Swelling of PU film, % | 23.00 | 64.50 | 36.10 | 57.20 | 22.00 | 32.56 | 28.63 | 30.90 | 32.60 | 20.30 |

TABLE 1-continued

Comparison of polyurethane batches. *Daily drug flux calculated using the mixing method, all others using the curve-fitting method

| | Lot# | | | | | | | | | |
|---|---|---|---|---|---|---|---|---|---|---|
| | 1100032 | 1100040 | 1100048 | 1100068 | 1100121 | 1100234 | 1100235 | 1100092 | 1100096 | 1100114 |
| Dry Elastic Modulus (+TFV, UC781) (MPa) | 14.4 ± 0.8 | 5.9 ± 0.3 | 6.3 ± 0.6 | 4.7 ± 0.1 | 15.9 ± 0.2 | 6.9 ± 0.3 | 13.7 ± 0.6 | 13.9 ± 0.8 | 10.7 ± 0.8 | 12.8 ± 2.4 |
| Swollen Elastic Modulus (+TFV, UC781) (MPa) | 4.9 ± 0.3 | 1.9 ± 0.0 | 3.0 ± 0.3 | 1.1 ± 0.1 | 6.3 ± 0.3 | 3.7 ± 0.3 | 5.0 ± 0.5 | 5.8 ± 0.5 | 4.3 ± 0.7 | 5.0 ± 1.0 |
| Extrusion Temp. (degree C.) | 155 | 140 | 140 | 132 | 125 | 128 | 134 | 152 | 155 | 152 |
| Mean Daily TFV Flux (µg/mm^2/d) | 9.6 | 18.3 | 2.3 | 23.2 | 6.9 | 3.6 | 5.1 | 5.5 | 10.1 | 5.5 |
| Mean Daily UC781 + UC22 Flux (µg/mm^2/d) | 2.4 | 2.8 | 2.6 | 1.9 | 2.7 | 4.3 | 3.7 | 2.5 | 2.9 | 2.7 |
| Swelling of PU rod formulated w/ TFV and UC781, % | 26 | 52 | 23 | 45 | 20 | 22 | 21 | 20 | 27 | 17 |
| Vk2 Cell Viability (Elution Assay) | Reduced | Reduced | Reduced | Reduced | No Change | 87% | 87% | Reduced | Reduced | Reduced |

TABLE 2

Process stability and accelerated stability study of lot#100032 + drugs with and without various antioxidants added based on Mw measured by GPC. Accelerated stability measured after 2.5 month.

| Sample ID | Polymer | Condition | Additives | Drugs | Mw | Mn | PDI |
|---|---|---|---|---|---|---|---|
| AT1-71A | 1100032 | Control | 0.05% EDTA, 1% CA | 20% TFV, 5% UC781 | 154702 | 86939 | 1.78 |
| AT1-71A | 1100032 | 40° C./75RH | 0.05% EDTA, 1% CA | 20% TFV, 5% UC781 | 165067 | 96121 | 1.72 |
| AT1-71A | 1100032 | 60° C. | 0.05% EDTA, 1% CA | 20% TFV, 5% UC781 | 165630 | 99753 | 1.66 |
| AT1-71B | 1100032 | Control | 0.5% Irganox | 20% TFV, 5% UC781 | 240213 | 117284 | 2.05 |
| AT1-71B | 1100032 | Control | 0.5% Irganox | 20% TFV, 5% UC781 | 230363 | 134108 | 1.72 |
| AT1-71B | 1100032 | 40° C./75RH | 0.5% Irganox | 20% TFV, 5% UC781 | 240148 | 122483 | 1.96 |
| AT1-71B | 1100032 | 60° C. | 0.5% Irganox | 20% TFV, 5% UC781 | 243252 | 126494 | 1.92 |
| AT1-76A | 1100032 | Control | 0.05% EDTA | 20% TFV, 5% UC781 | 217488 | 111033 | 1.97 |
| AT1-76A | 1100032 | 40° C./75RH | 0.05% EDTA | 20% TFV, 5% UC781 | 223410 | 117768 | 1.90 |
| AT1-76A | 1100032 | 60° C. | 0.05% EDTA | 20% TFV, 5% UC781 | 224090 | 116774 | 1.92 |
| AT1-76B | 1100032 | Control | 0.02% BHT | 20% TFV, 5% UC781 | 221380 | 117692 | 1.88 |
| AT1-76B | 1100032 | 40° C./75RH | 0.02% BHT | 20% TFV, 5% UC781 | 221680 | 112216 | 1.98 |
| AT1-76B | 1100032 | 60° C. | 0.02% BHT | 20% TFV, 5% UC781 | 224774 | 122294 | 1.84 |
| AT-1-72 | 1100032 | control | None | 20% TFV, 5% UC781 | 227744 | 127295 | 1.79 |

EDTA = ethylenediaminetetraacetic acid
CA = citric acid
IRGANOX = octadecyl-3-(3,5-di-tert.butyl-4-hydroxyphenyl)-propionate
BHT = butylated hydroxytoluene

TABLE 3

UC781 stability in Lot#1100032 with and without additives

| Sample ID | Polymer | Additives | Drugs |
|---|---|---|---|
| AT1-71A | 1100032 | 0.05% EDTA, 1% CA | 20% TFV, 5% UC781 |
| AT1-71B | 1100032 | 0.5% Irganox | 20% TFV, 5% UC781 |
| AT1-76A | 1100032 | 0.05% EDTA | 20% TFV, 5% UC781 |
| AT1-76B | 1100032 | 0.02% BHT | 20% TFV, 5% UC781 |
| JTC-C1-4 | 1100032 | None | 20% TFV, 5% UC781 |

TABLE 3-continued

UC781 stability in Lot#1100032 with and without additives

| Sample ID | Condition | UC 781 loading (mg/g) average | stdev | UC 781 % recovery average | stdev | UC 22 loading (mg/g) Average | stdev | % UC 22 | P value |
|---|---|---|---|---|---|---|---|---|---|
| AT1-71A | T = 0 | 50.51 | 1.03 | 100.00 | 2.04 | 0.04 | 0.00 | 0.08 | |
| AT1-71A | T = 4 weeks, 40° C. | 47.39 | 0.97 | 93.82 | 1.92 | 0.10 | 0.01 | 0.21 | 0.0012 |
| AT1-71A | T = 4 weeks, 60° C. | 45.55 | 0.65 | 90.18 | 1.30 | 0.17 | 0.01 | 0.38 | 0.0000 |
| AT1-71B | T = 0 | 53.01 | 0.93 | 100.00 | 1.76 | 0.06 | 0.01 | 0.11 | |
| AT1-71B | T = 4 weeks, 40° C. | 50.46 | 1.01 | 95.19 | 1.90 | 0.06 | 0.00 | 0.12 | 0.0060 |
| AT1-71B | T = 4 weeks, 60° C. | 50.06 | 1.08 | 94.44 | 2.03 | 0.10 | 0.02 | 0.20 | 0.0033 |
| AT1-76A | T = 0 | 48.31 | 0.84 | 100.00 | 1.74 | 0.09 | 0.01 | 0.18 | |
| AT1-76A | T = 4 weeks, 40° C. | 47.48 | 0.74 | 98.28 | 1.53 | 0.09 | 0.02 | 0.19 | 0.1365 |
| AT1-76A | T = 4 weeks, 60° C. | 49.58 | 0.94 | 102.61 | 1.95 | 0.14 | 0.05 | 0.28 | 0.1197 |
| AT1-76B | T = 0 | 54.18 | 1.34 | 100.00 | 2.48 | 0.07 | 0.02 | 0.14 | |
| AT1-76B | T = 4 weeks, 40° C. | 54.08 | 0.70 | 92.43 | 1.30 | 0.09 | 0.03 | 0.19 | 0.0009 |
| AT1-76B | T = 4 weeks, 60° C. | 52.29 | 0.73 | 96.50 | 1.35 | 0.07 | 0.02 | 0.14 | 0.0312 |
| JTC-C1-4 | T = 0 | 49.27 | 0.50 | 100.00 | 1.02 | | | | |
| JTC-C1-4 | T = 4 weeks, 40° C. | 49.11 | 0.40 | 99.67 | 0.81 | | | | 0.0857 |
| JTC-C1-4 | T = 4 weeks, 60° C. | 48.65 | 0.50 | 98.74 | 1.01 | | | | 0.5921 |

What is claimed is:

1. An intravaginal drug delivery device comprising:
a polyurethane copolymer having a number average molecular weight ranging from 50,000 to 350,000 g/mol and a swollen hardness of at least 30 A, the copolymer having the structure according to formula (I):

(I)

$$SME_1 \text{---} (HS \text{---} SS_1)_x \text{---} (HS \text{---} SS_2)_y \text{---} (HS \text{---} SS_3)_z \text{---} SME_2$$

wherein,
SS1, SS2, and SS3 denote soft segments, with SS1 being a polyether diol selected from polyethylene oxide (PEO) diol, polytetramethylene oxide (PTMO) diol, polyhexamethylene oxide diol (PHMO), polypropylene oxide (PPO) diol, copolymer of ethylene glycol and propylene glycol (PEG-co-PPO) diol, and mixtures thereof, SS2 being a hydroxyl or amine-terminated silicone polymer having a number average molecular weight ranging from 500 to 5000 g/mol, and SS3 being a soft-segment selected from polycarbonate diol and polyester diol and mixtures thereof,
HS denotes a hard segment comprising a diisocyanate selected from the group consisting of hexamethylene diisocyanate (HMDI) and isophorone diisocyanate (IPDI) and combinations thereof,
x and z are the same or different and each is an integer equal to or greater than zero, y is an integer equal to or greater than one, and at least two of x, y, and z are not zero; and
SME1 and SME2 can be the same or different and each denotes a surface modifying endgroup comprising a methyl polyethylene glycol (MPEG) having a number average molecular weight ranging from 200 to 8000, linked to the polymer via a urethane or urea bond resulting from the reaction of an amine- or alcohol-terminated surface modifying end group with an isocyanate group, and
at least one hydrophobic pharmaceutically active substance and at least one hydrophilic pharmaceutically active substance, said pharmaceutically active substances being homogenously distributed throughout the polyurethane copolymer.

2. The device according to claim 1, wherein
said at least one hydrophobic pharmaceutically active substance comprises a compound selected from the group consisting of dapivirine, UC781, valdecoxib, allopurinol, acetohexamide, benzthiazide, chlorpromazine, chlordiazepoxide, haloperidol, indomethacine, lorazepam, methoxsalen, methylprednisone, nifedipine, oxazepam, oxyphenbutazone, prednisone, prednisolone, pyrimethamine, phenindione, sulfisoxazole, sulfadiazine, temazepam, sulfamerazine, and trioxsalen, and
said at least one hydrophilic pharmaceutically active substance comprises a compound selected from the group consisting of 17β-estradiol, acyclovir, estriol, raloxifene, pravastatin, atenolol, aminoglycosides, polysaccharide, cyclodextrins, and chitosan.

3. The device according to claim 1, wherein the mean daily flux of at least one of the pharmaceutically active substances is greater than 0.1 μg/mm²/d.

4. The device according to claim 1, wherein the polyurethane copolymer is capable of absorbing water up to 50% by weight related to the total weight of the dry copolymer.

5. The device according to claim 1, wherein the polyurethane composition is made by a process wherein the catalyst stannous octoate is used.

6. The device according to claim 1, further comprising antioxidants.

7. The device according to claim 1, wherein the polymer is non-cytotoxic.

8. A method for administering one or more pharmaceutically active substances to a patient in need thereof, comprising inserting the device of claim 1 into the patient, whereby the active substance is released from the delivery device while the device resides in the patient's body.

9. The device according to claim 1, wherein the percentage of the silicone soft segment is up to 40 weight % of the total weight of the polyurethane copolymer.

10. The device according to claim 1, wherein the percentage of the silicone soft segment is up to 20 weight % of the total weight of the polyurethane copolymer.

* * * * *